(12) United States Patent
Lee et al.

(10) Patent No.: US 6,905,470 B2
(45) Date of Patent: Jun. 14, 2005

(54) APPARATUS AND METHOD FOR DETECTING HEARTBEAT USING PPG

(75) Inventors: Mi Hee Lee, Kyungki-do (KR); Seok Won Bang, Seoul (KR); Kyung Hwan Kim, Kyungki-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 50 days.

(21) Appl. No.: 10/413,149

(22) Filed: Apr. 15, 2003

(65) Prior Publication Data

US 2003/0212336 A1 Nov. 13, 2003

(30) Foreign Application Priority Data

Apr. 15, 2002 (KR) .................................. 10-2002-0020353

(51) Int. Cl.[7] .............................. A61B 5/02; A61B 5/00
(52) U.S. Cl. ...................... 600/500; 600/501; 600/310; 600/322
(58) Field of Search .................................. 600/500–503, 600/481, 483, 485, 508, 473, 476, 479, 480, 310, 322–324

(56) References Cited

U.S. PATENT DOCUMENTS

| 4,800,495 | A | * | 1/1989 | Smith | .......................... 600/322 |
| 5,365,934 | A | | 11/1994 | Leon et al. | |
| 5,738,104 | A | | 4/1998 | Lo et al. | |
| 6,002,952 | A | | 12/1999 | Diab et al. | |
| 6,067,462 | A | * | 5/2000 | Diab et al. | ................... 600/310 |
| 6,135,966 | A | * | 10/2000 | Ko | .............................. 600/481 |

FOREIGN PATENT DOCUMENTS

| JP | 11-9564 | 1/1999 |
| JP | 2000-217796 | 8/2000 |
| WO | 00/22408 | 4/2000 |
| WO | 00/38569 | 7/2000 |

OTHER PUBLICATIONS

Coetzee, F., *Noise–Resistant Pulse Oximetry Using a Synthetic Reference Signal*, IEEE Transactions on Biomedical Engineering, vol. 47, No. 8, Aug. 2000, pp. 1018–1026.

Lee. J.W., et al., *Signal Processing of the Pulse Oximeter to Eliminate the Motion Artifact*, 24th Spring Conference of the Korea Society of Medical and Biological Engineering, vol. 24, No. 1, May 2001, pp. 123–124.

European Search Report issued by the European Patent Office on Aug. 18, 2003 for corresponding application EP 03252406.

Office Action issued by the European Patent Office on Apr. 28, 2004 for corresponding application EP 03252406.8.

* cited by examiner

*Primary Examiner*—Robert L. Nasser
*Assistant Examiner*—Navin Natnithithadha
(74) *Attorney, Agent, or Firm*—Burns, Doane, Swecker & Mathis, L.L.P.

(57) ABSTRACT

The present invention relates to an apparatus and method capable of detecting a heartbeat using a photoplethysmography (PPG) even under a motion of a user. A primary object of the present invention is to allow the heartbeat of the user to be effectively detected from a PPG signal even under the motion. The object of the present invention is accomplished by the following process of acquiring the PPG signal from the user through a PPG sensor unit, detecting candidate heartbeat sequences from the PPG signal after calculating an expected mean interbeat interval through a signal processing technique based on the wavelet transformation and an auto-correlation function, and extracting an optimal heartbeat sequence or mean heart rate from the candidate heartbeat sequences.

25 Claims, 11 Drawing Sheets

APPARATUS AND METHOD FOR DETECTING HEARTBEAT USING PPG

This application claims the priority of Korean Patent Application No. 10-2002-0020353, filed on Apr. 15, 2002, in the Korean Intellectual Property Office, the disclosure of which is incorporated herein in its entirety by reference.

BACKGROUND OF THE INVENTION

1. Field of the Invention

The present invention relates to an apparatus and method for detecting a heartbeat, and more particularly, to an apparatus and method for detecting a heartbeat by using a photoplethysmography (PPG) which is capable of detecting the heartbeat even under motion of a user, i.e. is hardly influenced by any motion artifact.

2. Description of the Prior Art

In general, a PPG is a method of extracting information related to a heartbeat by using a predetermined number of LEDs and optical sensors. According to the method of detecting the heartbeat using the PPG, the heartbeat can be detected through a simple sensor which is attached to only one contact point of a human body. Thus, the PPG-based method is more convenient to a user than an electrocardiogram (ECG) method in which at least two electrodes should be used, and it can be much more efficiently applied to a medical or non-medical purpose instrument. On the other hand, the PPG-based method has a disadvantage in that a large amplitude of the motion artifact is induced into a PPG signal even under any slight motion of the user. Such a motion artifact can be defined as a noise signal generated by a slight motion such as a minute quiver of the human body upon detection of the heartbeat. Therefore, in order to obtain a highly reliable heartbeat measurement, the motion artifact should be eliminated from the resultant PPG signal.

Heartbeat detection has been widely used in various fields for medical or non-medical purposes. As a typical method for detecting the heartbeat, there has been provided a method (electrocardiogram) of measuring and recording a value of an active current generated due to contraction and/or relaxation of a heart muscle by using electrodes attached onto predetermined parts of a human body.

However, the conventional heartbeat detection apparatus has problems in that the user is reluctant to use the apparatus since the electrodes are attached to or bands are bound around the human body, and in that it is very inconvenient for the user to use the apparatus unless the user has considerable knowledge of its use.

In order to solve these problems, there has been proposed a circulatory function diagnostic device disclosed in Japanese Patent Laid-Open Publication No. 2000-217796 (date of publication: Aug. 8, 2000), which can easily diagnose a function of the blood circulatory system using a waveform pattern of an acceleration pulse wave obtained by detecting a pulse wave generated from blood pulsation through a PPG measuring means and differentiating the detected pulse wave twice. The circulatory function diagnostic device has an advantage in that it can be used without any relevant special knowledge. However, the circulatory function diagnostic device has not yet proposed a solution against the motion artifact.

In addition, Japanese Patent Laid-Open Publication No. 1999-9564 (date of publication: Jan. 19, 1999) discloses a cardiac function diagnosing apparatus for diagnosing a cardiac function by using a heart rate obtained through various pulse wave detecting means (a photoelectric pulse wave sensor, a PPG sensor and a pressure sensor), a frequency analysis result of heart rate variability thereof, and characteristic points of the twice-differentiated PPG. The cardiac function diagnosing apparatus is formed into a glass type, a necklace type and a watch type, and also utilizes an acceleration sensor for warning the motion of the user. However, there is still a disadvantage in that it is impossible to detect the heartbeat even while the user is moving.

Furthermore, there has been published the following technical papers on the removal of motion artifacts in the PPG in the field of a pulse oximeter used for measuring a blood oxygen concentration by irradiating two specific wavelengths of light onto a finger or ear.

Figure 1:
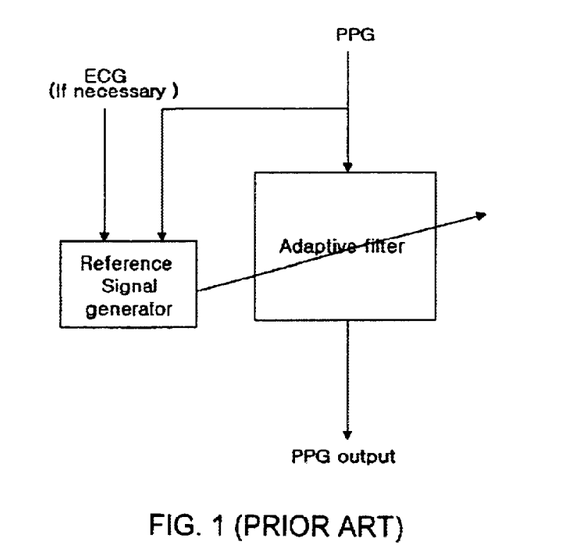
FIG. 1 is a view illustrating a method of eliminating noise from a conventional pulse oximeter by using a composite reference signal.

In the technical paper ("Noise resistance pulse oximetry using composite reference signal", IEEE Trans. Biomed. Eng., Vol. 47, No. 8, 2000. 8) is disclosed a method of eliminating noise (i.e., motion artifact) by estimating a composite reference signal from a noise-free PPG signal (or ECG signal) and comparing the composite reference signal with the PPG signal inputted through an adaptive filter, as shown in FIG. 1. However, such a method of eliminating the noise has a limitation in that the ECG signal should ultimately be used as the reference signal since the reliability thereof is determined depending on estimation accuracy of the reference signal.

Figure 2:
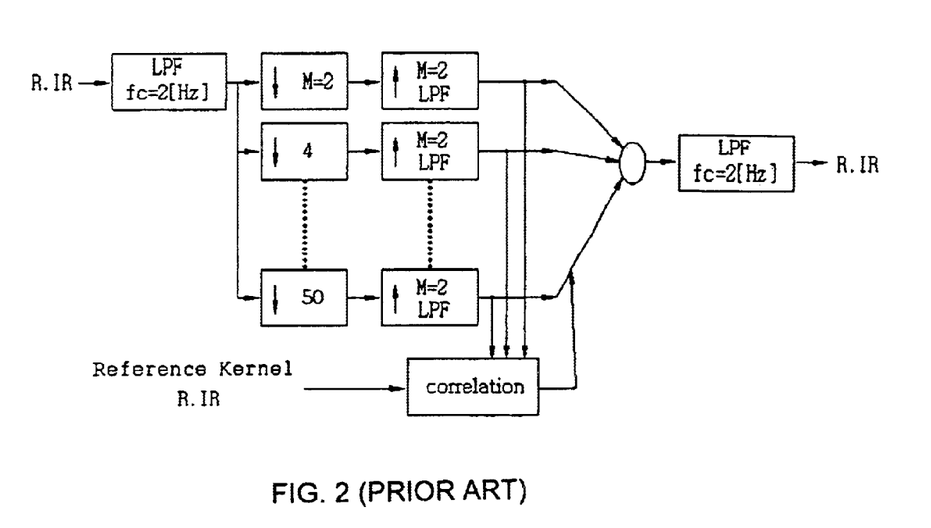
FIG. 2 is a view illustrating a method of eliminating motion artifacts from the conventional pulse oximeter.

In another technical paper ("Signal processing in the pulse oximeter for eliminating the motion artifact", 24th Spring Conference of the Korea Society of Medical and Biological Engineering, Vol. 24, No. 1, May 25 and 26, 2001) is disclosed a method of eliminating the motion artifact by passing a signal having a greatest value of correlation through a low pass filter after calculating the correlation between a signal outputted to each of respective banks and the reference signal in order to measure highly reliable oxygen concentration even under the user's motion, as shown in FIG. 2. However, considering that the motion artifact includes both high and low frequency components, the elimination of the motion artifact through the low pass filter is not very effective.

SUMMARY OF THE INVENTION

Accordingly, the present invention is contemplated to solve the above problems in the prior arts. An object of the present invention is to allow a heartbeat to be effectively detected under a motion artifact and an influence of the motion artifact, which is one of critical problems upon use of a PPG, to be suppressed to the utmost.

Another object of the present invention is to improve reliability of heartbeat detection by not using a reference signal substantially difficult to estimate.

A further object of the present invention is to provide a method of detecting a heartbeat wherein if a motion artifact is greater than a threshold value measured previously, it is simply informed of a user; and only if the motion artifact is equal to or lower than the threshold value, a time when a heartbeat is generated and a mean heart rate during an interval of the time should be outputted based on the PPG signal.

In order to achieve the above objects of the present invention, there is provided an apparatus for detecting a heartbeat using a photoplethysmography (PPG), comprising a sensor unit for detecting a PPG signal from a body of a user, a mean interbeat interval estimating unit for calculating an expected mean interbeat interval based on the detected PPG signal, and a heartbeat sequence/mean heart rate extracting unit for detecting candidate heartbeat sequences from the PPG signal using the expected mean interbeat interval and extracting more precise mean heart rate by informing or estimating when the respective heartbeats occur based on an optimal heartbeat sequence estimated from the candidate heartbeat sequences.

Preferably, the apparatus of the present invention further may comprise a filtering unit for selectively passing only a signal within a specific frequency band among the PPG signal detected by the PPG sensor unit.

Preferably, the apparatus of the present invention may further comprise a motion artifact level determining unit for determining a level of a motion artifact in the PPG signal based on the PPG signal detected from the PPG sensor unit so that a warning message is produced when the level of the motion artifact is greater than a predetermined threshold value.

Preferably, the apparatus of the present invention may further comprise a display unit for causing both the optimal heartbeat sequence or mean heart rate extracted from the heartbeat sequence/mean heart rate extracting unit and the warning message produced from the motion artifact level determining unit to be displayed thereon.

In order to achieve the objects of the present invention, there is also provided a method of detecting a heartbeat using a photoplethysmography (PPG), comprising the steps of detecting a PPG signal received from a user through a PPG sensor unit, calculating an expected mean interbeat interval (mean IBI) from the PPG signal, and detecting determining an optimal heartbeat sequence or mean heart rate from candidate heartbeat sequences which have been detected from the PPG signal using the expected mean interbeat interval.

Preferably, the method of present invention may further comprise a filtering step of selectively passing only a signal within a specific frequency band among the PPG signal detected by the PPG sensor unit.

Preferably, the method of present invention may further comprise the step of determining a level of a motion artifact based on the. PPG signal detected from the PPG sensor unit and then generating a warning message when the level of the motion artifact is greater than a predetermined threshold value.

Preferably, the method of the present invention may further comprise the step of displaying the detected optimal heartbeat sequence or mean heart rate and the warning message on a screen.

BRIEF DESCRIPTION OF THE DRAWINGS

The above and other objects and features of the present invention will become apparent from the following description of a preferred embodiment given in conjunction with the accompanying drawings, in which.

DETAILED DESCRIPTION FOR PREFERRED EMBODIMENT

Hereinafter, the constitution and operation of an apparatus for detecting a heartbeat by using PPG according to the present invention will be explained in detail with reference to the accompanying drawings.

Figure 3:
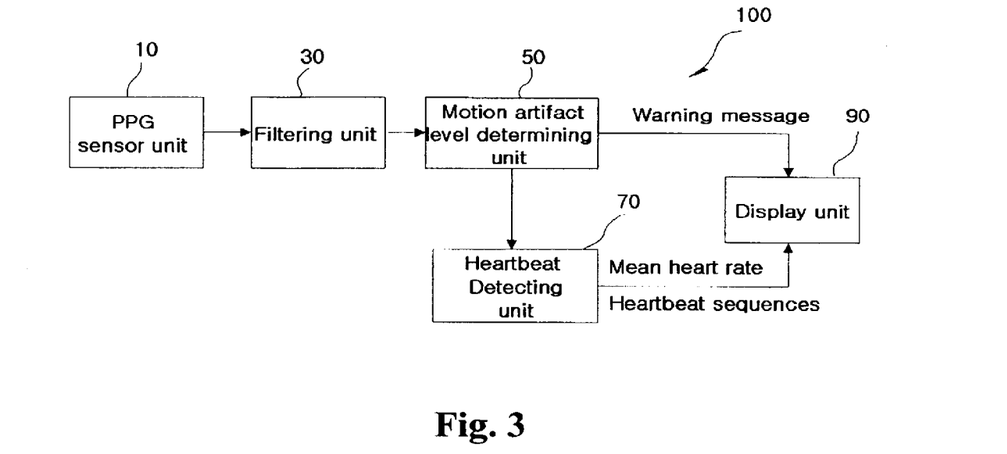
FIG. 3 is a block diagram schematically showing an apparatus for detecting heartbeat according to the present invention.

FIG. 3 shows a block diagram schematically illustrating the apparatus 100 for detecting the heartbeat according to the present invention. The heartbeat detection apparatus comprises a PPG sensor unit 10, a filtering unit 30, a motion artifact level determination unit 50, a heartbeat detection unit 70, and a display unit 90.

Figure 12:
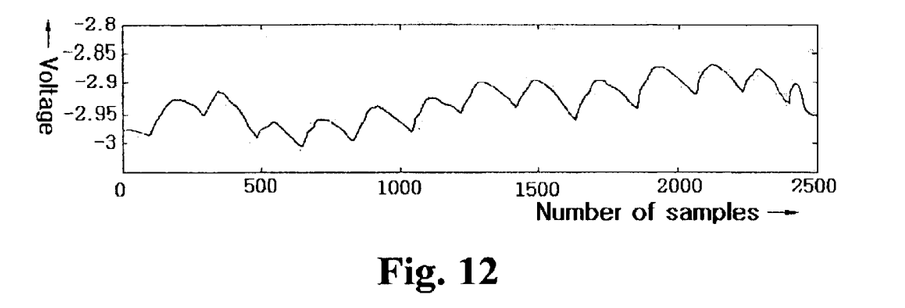
FIG. 12 is a waveform graph illustrating a PPG signal detected by a PPG sensor unit.

The PPG sensor unit 10 uses a principle that a degree of absorption and reflection of light varies according to a change in thickness resulting from the heartbeat, and includes a light emitting part (not shown) for emitting infrared rays and a light receiving part (not shown) for sensing light which is irradiated onto a body of a user from the light emitting part and reflected to the light receiving part. Further, the PPG sensor unit detects a PPG signal based on an optically measured blood flow rate outputted from the light emitting part and outputs it to the filtering unit 30, as shown in FIG. 12.

Figure 13:
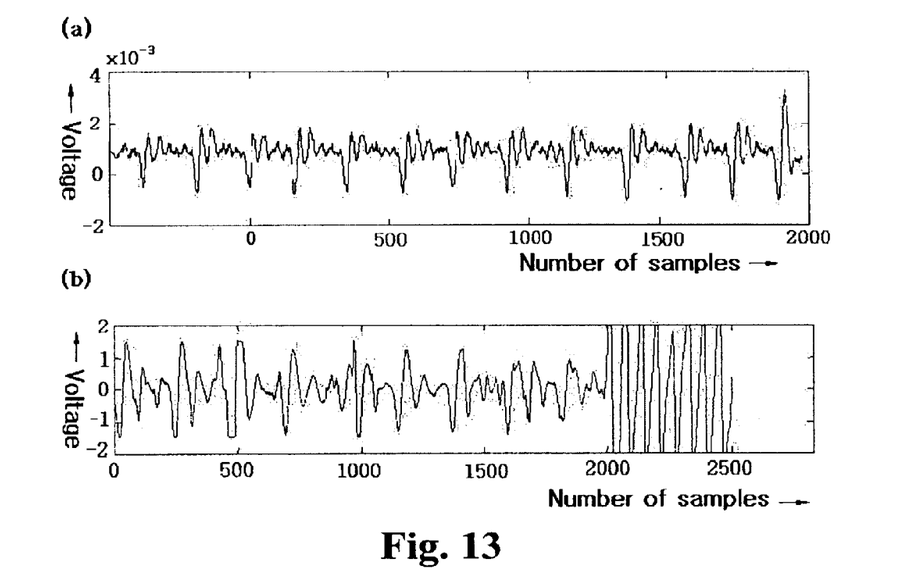
FIG. 13(a) is a waveform graph of a PPG signal with the motion artifacts being not included therein, which passed through a filtering unit.
FIG. 13(b) is a waveform graph of a PPG signal with the motion artifacts being included therein, which passed through the filtering unit.

The filtering unit 30 performs a function of selectively passing only a signal component related to the heartbeat among the PPG signal detected by the PPG sensor unit 10. An example of a PPG signal waveform passed through the filtering unit 30 is shown in FIG. 13. Preferably, the filtering unit 30 may be implemented as a bandpass filter or a second-order differential filter.

Meanwhile, in FIGS. 12 to 19, the X-axis and Y-axis represent the number of sample and a voltage, respectively. Further, the number of samples represented in the X-axis can be substituted for a time $X_t$ in accordance with the following relationship:

$$Xt = (\text{number of samples})/(\text{sampling frequency})$$

In the present invention, since a case where the sampling frequency is 25 Hz will be explained as an example, the numbers of samples, i.e. 500, 1000, 1500, 2000, 2500 and 3000 represented in the X-axis of FIGS. 12 to 19 can be converted into the time, i.e. 20, 40, 60, 80, 100 and 120 seconds, respectively.

Figure 4:
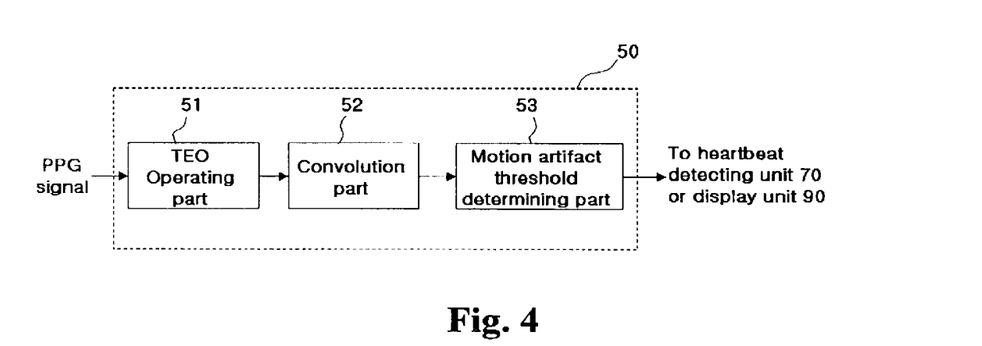
FIG. 4 is a view showing an internal structure of a motion artifact level determination unit shown in FIG. 3.

FIG. 4 shows and internal structure of the motion artifact level determination unit 50 shown in FIG. 3. The motion artifact level determination unit 50 includes a Teager Energy Operator (TEO) operating part 51, a convolution part 52 and a motion artifact threshold measurement part 53. The motion artifact threshold determination unit is constructed to output the filtered PPG signal to the heartbeat detection unit only when the motion artifacts are equal to or lower than a predetermined threshold.

The TEO operating part 51 uses a phenomenon that an amplitude and frequency of the signal are instantaneously increased greatly when the motion artifacts are severe. That is, the TEO operating part 51 detects an interval where the motion artifacts occurred among the PPG signal outputted from the filtering unit 30, by calculating a sudden rate of change in the amplitude and frequency of the PPG signal using TEO-based operation.

The convolution part performs the convolution of the PPG signal outputted from the TEO operating part 51 with a Bartlett window function so that a TEO output signal can be smoothed.

Figure 14:
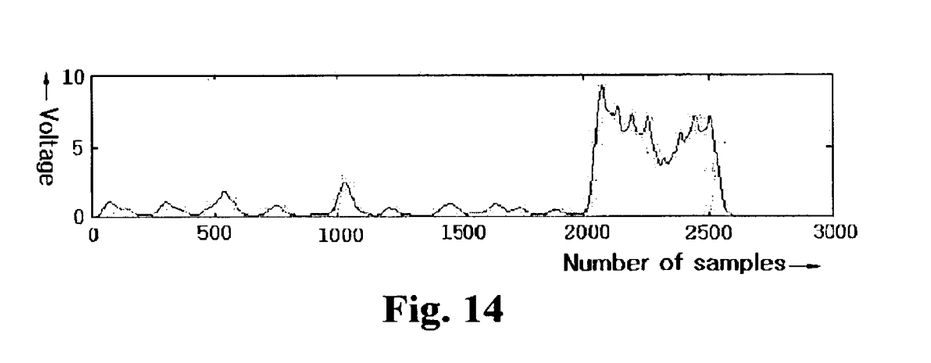
FIG. 14 is a waveform graph of a PPG signal passed through a TEO-based operation unit and a convolution unit.

An example of a waveform of the PPG signal, which has passed through the TEO operating part 51 and the convolution part 52, is shown in FIG. 14. In a case where the PPG signal passed through the filtering unit 30 includes the motion artifact (refer to FIG. 13 (b)), it will be understood from the figure that a waveform having a large amplitude is outputted at the interval in which the severe motion artifacts are included, by performing the TEO operation of the PPG signal and then the convolution of the signal with the Bartlett window function.

As mentioned above, the TEO operating part 51 and the convolution part 52 are preprocessing modules for allowing a level of the motion artifact included in the PPG signal outputted from the filtering unit 30 to be easily determined. If necessary, they may be removed so as to simplify the construction of the apparatus.

In order to determine the level of the motion artifact included in the PPG signal, a predetermined value obtained by multiplying a TEO output value $TEO_{output}$ in the interval including a normal heartbeat signal by a proper value is first set as the predetermined threshold. Then, when the PPG signal having the amplitude larger than the threshold is outputted, the motion artifact threshold measurement part 53 recognizes that the level of the motion artifact is beyond an allowable range and causes a warning message to be displayed onto the display unit 90. Otherwise, the motion artifact threshold measurement part 53 recognizes that the level of the motion artifact is within the allowable range and outputs the PPG signal from the filtering unit 30 to the heartbeat detection unit 70.

Figure 5:
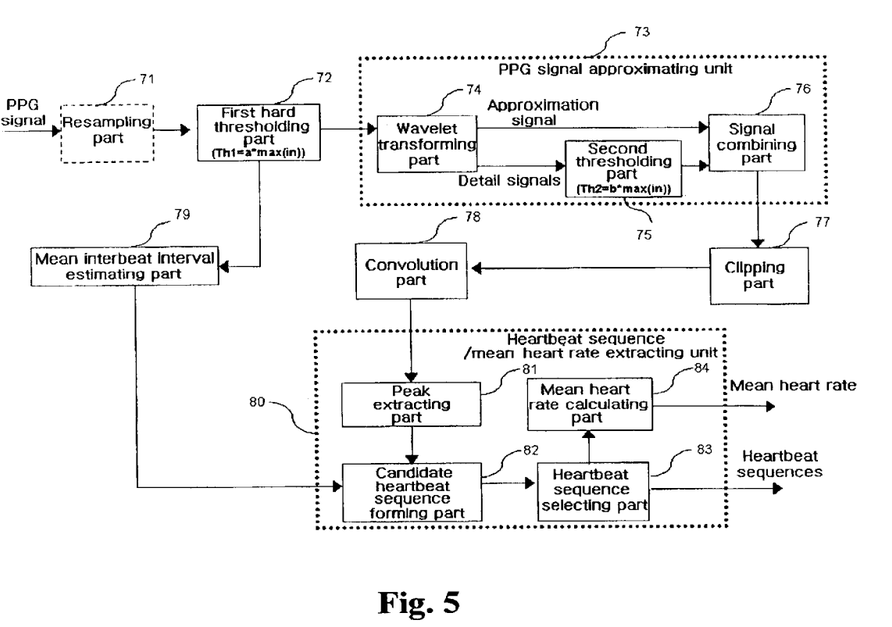
FIG. 5 is a view showing an internal structure of a heartbeat detection unit shown in FIG. 3.

FIG. 5 shows an internal structure of the heartbeat detection unit 70 shown in FIG. 3, which includes a resampling part 71, a first hard thresholding part 72, a PPG signal approximating unit 73, a clipping part 77, a convolution part 78, a mean interbeat interval estimating part 79, and a heartbeat sequence/mean heart rate extracting unit 80.

The resampling part 71 samples again the signal inputted from the PPG sensor unit 10 for performing rapid signal processing when the sampling frequency of the PPG signal is higher than needed (hereinafter, referred to as "resampling process"), and the first hard thresholding part 72 performs a hard thresholding process of the resampled PPG signal into a predetermined level so that undesired peaks of the signal lower than the predetermined level can be removed. The resampling part 71 may be removed so as to simplify the construction of the apparatus. Here, the hard thresholding process is a process in which the input signal is compared with the thresholding level, a signal value lower than the thresholding value is replaced by zero, and a signal value greater than the thresholding value is kept unchanged.

The PPG signal approximating unit 73 performs a function of approximating the PPG signal by removing a high frequency noise through a wavelet transformation, and includes a wavelet transforming part 74, a second hard thresholding part 75, and a signal combining part 76.

The wavelet transforming part 74 performs a function of decomposing the PPG signal into an approximation signal component representing an overall waveform of the PPG signal and a detail signal component after wavelet transforming the PPG signal inputted from the first hard thresholding part 72, and an example thereof is shown in FIG. 15(a). As shown in FIG. 15(a), the PPG signal is decomposed into the detail components d1, d2, d3, d4 and d5 and the approximation signal component a5 through the wavelet transformation.

The second hard thresholding part 75 substitutes zero value for the components having smaller amplitude and extracts only the components having greater amplitude, among the detail signal components d1, d2, d3, d4 and d5 generated through the wavelet transformation. Thus, the high frequency noise is removed.

Here, in order to obtain only the signal components related to the heartbeat, the detail signal components in a generally high frequency region (e.g., d1, d2, d3 and d4) are ignored as an undesired signal, the component having the greater amplitude can be extracted only from the detail signal component related to a subtle change in the heartbeat (e.g., d5).

The signal combining part 76 combines the approximation signal generated through the wavelet transformation with the detail signal subjected to the hard thresholding process, and outputs the approximated PPG signal to clipping part 77.

An example of a PPG signal waveform outputted from the PPG signal approximating unit 73 is shown in FIG. 15(b). As shown in the figure, the approximated PPG signal with the high frequency components removed therefrom can be obtained by combining the approximation signal generated through the wavelet transformation with the detail signal subjected to the hard thresholding process. Thus, the approximated signal has discontinuous points since the detail signal has been subjected to the hard thresholding process.

To this end, the clipping part 77 passes through positive values of the approximated PPG signal and substitutes zero value for negative values thereof, and outputs only the signal components related to the heartbeat, i.e. positive peaks related to the heartbeat to the convolution part 78. The convolution part 78 causes the zero clipped PPG signal to be smoothed by performing the convolution of the PPG signal with the Bartlett window function so that the discontinuous points obtained in the approximation process can be removed.

An example of a PPG signal waveform with the discontinuous points removed therefrom through the convolution process is shown in FIG. 16(a). As shown in the figure, the modified signal inputted from the convolution part 78 to the heartbeat sequence/mean heart rate extracting unit 80 contains only the heartbeat related signal components, and the discontinuous points are also removed from the modified signal. Thus, the peaks produced by the heartbeat can be easily detected from the modified signal.

The heartbeat sequence/mean heart rate extracting unit 80 performs a function of suppressing an influence of the motion artifact upon detection of the heartbeat, and comprises a peak extracting part 81, a candidate heartbeat sequence forming part 82, a heartbeat sequence selecting part 83, and a mean heart rate calculating part 84.

The peak extracting part 81 detects all the peaks existing in an initial interval (about two-second interval) of the PPG signal inputted from the convolution part 78. The peak detection is accomplished in such a manner that an original signal is differentiated and zero-crossing points are then found. As shown in FIG. 16(b), since other peaks having the large amplitude instantaneously increased by the motion artifact are detected simultaneously upon detection of the peaks of the PPG signal, an additional process of distinguishing the peaks due to the motion artifact and the heartbeat is also required.

To this end, in the present invention, an optimal heartbeat sequence is selected among several candidate heartbeat sequences starting respectively from the peaks extracted from the initial interval of the PPG signal, so that the influence of the motion artifact can be suppressed to the utmost. Since it will be described in detail with reference to FIG. 9, it is now explained briefly.

The candidate heartbeat sequence forming part 82 forms a plurality of candidate heartbeat sequences by setting the peaks within the initial interval as the starting points and sequentially detecting peaks existing in the vicinity of an expected mean interbeat interval (expected mean interbeat interval±ΔT), and selects window signals of which centers are positioned at a time spaced apart by the expected means interbeat interval from the same starting points as the candidate heartbeat sequences.

The heartbeat sequence selecting part 83 multiplies the respective candidate heartbeat sequences by the window signals, adds up all the multiplied values, scores the added values, and selects a candidate heartbeat sequence having a maximum scored value as an optimal heartbeat sequence. Then, the selecting part displays the optimal heartbeat sequence onto the display unit 90 or outputs it to the mean heart rate calculating part 84 for calculating a mean heart rate within a predetermined interval.

The aforementioned method of selecting the optimal heartbeat sequence among the candidate heartbeat sequences is as follows (refer to FIG. 17). First, the window signals and candidate heartbeat sequences having the same starting points as each other are multiplied by each other, the respective values obtained as such are added up together, and all the added values are finally scored. Then, the candidate heartbeat sequence having the maximum scored value is selected as the optimal heartbeat sequence (a second candidate sequence in FIG. 17). Here, solid and dashed arrows and trapezoids correspond to the times spaced apart by the expected mean interbeat interval from the starting points of the two candidate heartbeat sequences and window signals of which centers are positioned at the times, respectively.

From the foregoing, the expected mean interbeat interval is obtained from the mean interbeat interval estimating part 79, which will be explained more specifically with reference to FIG. 6.

Figure 6:
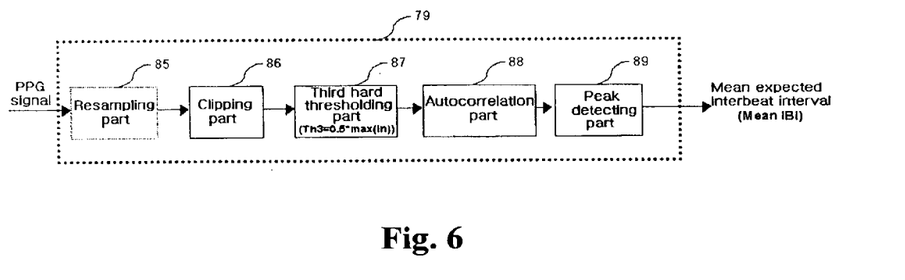
FIG. 6 is a view showing an internal structure of a mean interbeat interval estimation unit shown in FIG. 5.

FIG. 6 shows an internal structure of the mean interbeat interval estimating part 79 shown in FIG. 5. The means interbeat interval estimating part 79 outputs the expected mean interbeat interval needed for extracting the heartbeat sequence and includes a resampling part 85, a clipping part 86, a third hard thresholding part 87, an autocorrelation part 88, and a peak detecting part 89.

The mean interbeat interval estimating part 79 estimates the mean interbeat interval based on a method of estimating a mean pitch within the interval in the speech processing. In particular, in order to minimize any errors due to noise, the expected mean interbeat interval is estimated after the noise has been removed through the resampling, clipping, hard thresholding and autocorrelation functions.

If the resampling part 85 decreases a sampling rate (sampling frequency) by resampling the inputted PPG signal, the clipping part 86 outputs the positive peaks of the PPG signal due to the heartbeat through zero clipping of the resampled PPG signal. Then, the third hard thresholding part 87 removes small peaks due to the motion artifacts by performing the hard thresholding of the clipped PPG signal, i.e. the positive peak signals due to the heartbeat on the basis of a predetermined level.

The autocorrelation part 88 uses a principle that if the autocorrelation function of the input signal is obtained, a nonperiodical signal component such as noise (random noise) converges to zero while a periodical signal component has a large amplitude value at a time corresponding to its own period or a value obtained by integer-times value. That is, the autocorrelation part 88 can calculate the autocorrelation function of the hard thresholded PPG signal and detect the period of the periodical signal without being influenced by the noise.

Figure 18:
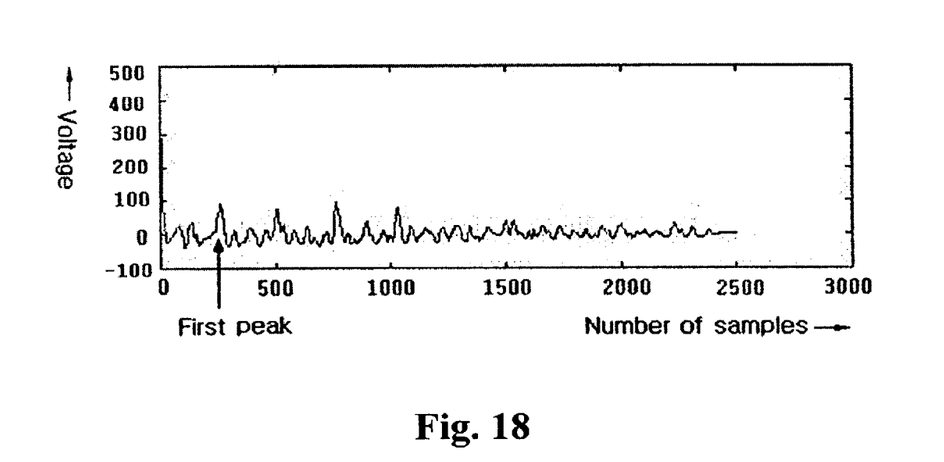
FIG. 18 is a waveform graph of a PPG signal outputted from a mean interbeat interval estimation unit.

An example of the autocorrelation function outputted from the autocorrelation part 88 is shown in FIG. 18. As shown in the figure, if the autocorrelation function of the PPG signal is calculated, the autocorrelation function has the peaks at points corresponding to the period of the heartbeat. Thus, the expected period of the heartbeat can be easily detected.

The peak detecting part 89 detects a time when a first peak occurred in the autocorrelation function of the PPG signal, and estimates it as the expected mean interbeat interval. Further, the candidate heartbeat sequence forming part 82 detects the peaks from only the intervals having a higher heartbeat occurring probability based on the expected mean interbeat interval, and forms the plurality of the candidate heartbeat sequences. Thus, the candidate heartbeat sequences can be extracted in short time.

The display unit 90 performs a function of displaying the heartbeat sequences or mean heart rate of the user onto a display screen, and acquires information on characteristics of the heart rate in a time or frequency domain through a heart rate variability analyzer (HRV analyzer) to display the information to the user.

Hereinafter, a method of detecting the heartbeat using the PPG according to the present invention will be explained in detail with reference to the accompanying drawings.

Figure 7:
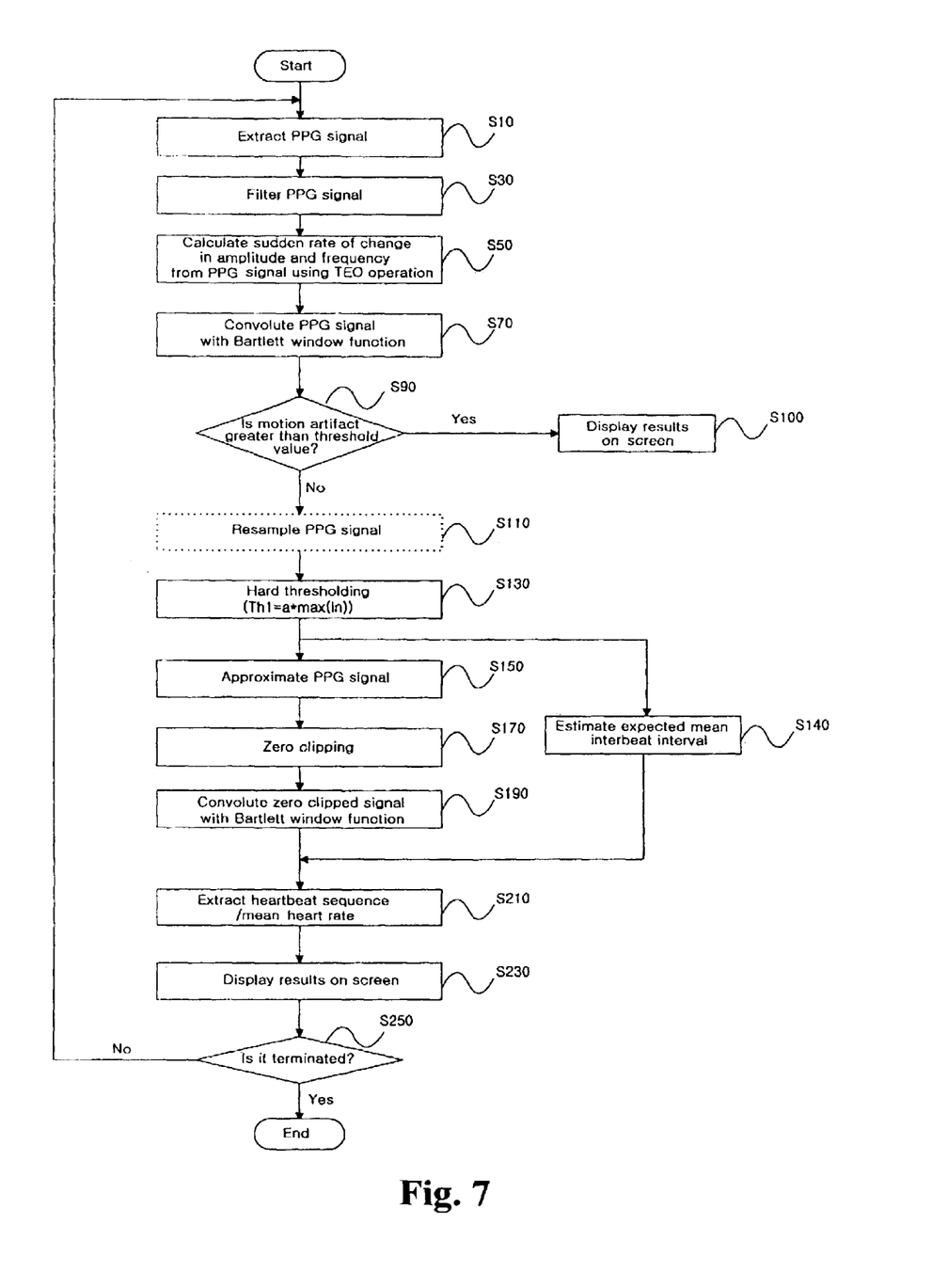
FIG. 7 is a flowchart illustrating a method for detecting heartbeat according to the present invention.

FIG. 7 shows a flowchart illustrating an embodiment of the method of detecting the heartbeat according to the present invention.

First, if the PPG signal is detected from the PPG sensor unit 10 (refer to FIG. 12), only the heartbeat related signal components in the detected PPG signal is caused to be filtered out from the filtering unit 30 (steps S10 and S301, refer to FIG. 13).

Then, in order to detect the intervals where the motion artifacts occurred from the PPG signal that has been outputted from the filtering unit 30, the sudden rate of change in the amplitude and frequency of the inputted PPG signal is extracted by using the TEO operation (step S50). Here, a formula related to the TEO operation is expressed as the following equation (1).

$$(x(t)) = \left(\frac{dx(t)}{dt}\right)^2 - x(t)\left(\frac{d^2 x(t)}{dt^2}\right) \tag{1}$$

As expressed in the equation (1), the TEO operation is used to calculate the output which is proportional to a square of a product of an instantaneous amplitude and an instantaneous frequency of the inputted signal and extracts the sudden rate of change in the amplitude and frequency in the PPG signal, so that the intervals where the motion artifacts occurred can be detected.

Then, the PPG signal subjected to the TEO operation is convoluted with the Bartlett window function so that the PPG signal is smoothed (step S70). It is checked whether the level of the motion artifact thereof is greater than the threshold value by performing the hard thresholding process of the smoothed PPG signal on the basis of a predetermined level suitable for the TEO output value within the interval where the normal heartbeat signal exists (S90). Here, a hard thresholding level is expressed as the following equation (2).

$$\text{Threshold} = 3 \times \max(TEO_{output}) \tag{2}$$

In the present embodiment, the hard thresholding level for checking whether the level of the motion artifact is greater than the threshold level has been set as a three-times value of a maximum value of the TEO output value within the interval where the normal heartbeat signal exists. If the signal greater than the threshold value is detected, it is regarded that the signal contains the severe motion artifacts therein, and thus, the heartbeat detection can be performed no longer.

If it is determined by the hard thresholding process that the signal contains the severe motion artifacts, the warning message is displayed onto the display unit 90 (step S100). Otherwise, it is considered that the level of the motion artifacts of the signal is within the allowable range, and then, it goes into a heartbeat detection step.

Therefore, in the steps (steps S50 to S100) of determining the level of the motion artifact of the signal, the heartbeat is detected only when the motion artifacts are equal to or lower than the threshold value. Furthermore, when the motion artifacts are greater than the threshold, the user is informed of this condition so that the motion of the user can be reduced.

Thereafter, the pre-processing of resampling the PPG signal for rapid signal processing is performed (step S110), and then, the resampled PPG signal is subject to the hard thresholding on the basis of the suitable level to remove the undesired PPG signal (step S130). In the embodiment, a hard thresholding level is expressed as the following equation (3).

$$Th1 = a \times \max(\text{input}) \tag{3}$$

In the embodiment, the hard thresholding level Th1 has been set as a value which is a-times value of the maximum value among the PPG signal in the interval, where a is lower than 0.4. Further, since the signal lower than the hard thresholding level Th1 is not a peak due to the heartbeat, it is ignored and removed as an undesired signal.

Next, the PPG signal is approximated by removing the high frequency noise of the PPG signal using the wavelet transformation (step S150). The approximation of the PPG signal will be more specifically described hereinafter with reference to FIG. 8.

Figure 8:
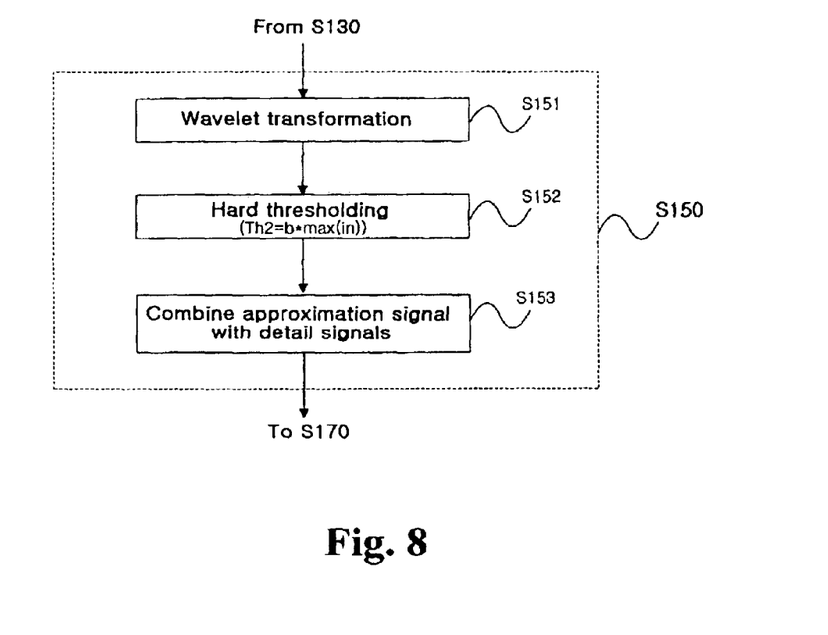
FIG. 8 is a detailed flowchart illustrating a step of approximating PPG signals shown in FIG. 7.
Figure 15:
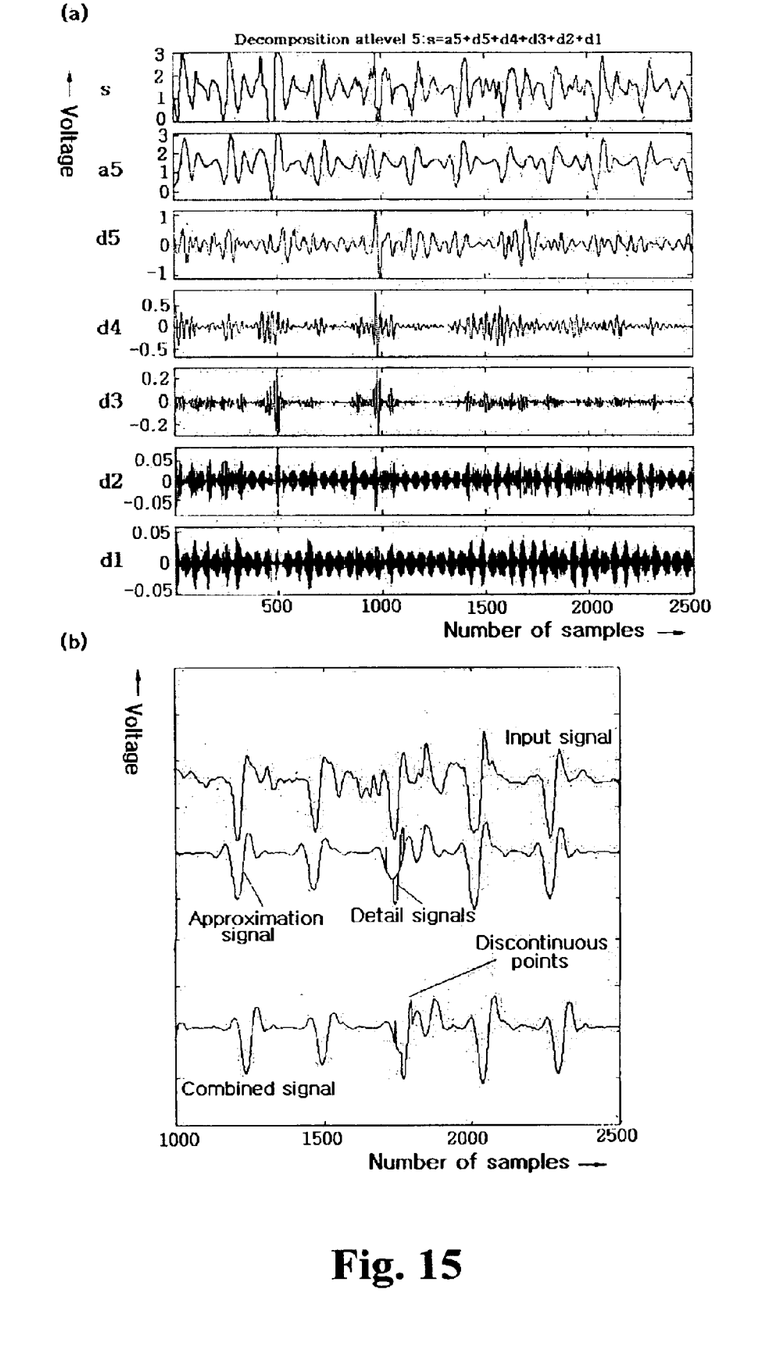
FIG. 15(a) is a waveform graph of a PPG signal outputted from a wavelet transformation unit.
FIG. 15(b) is a waveform graph of a PPG signal outputted from a PPG signal approximation unit.
Figure 16:
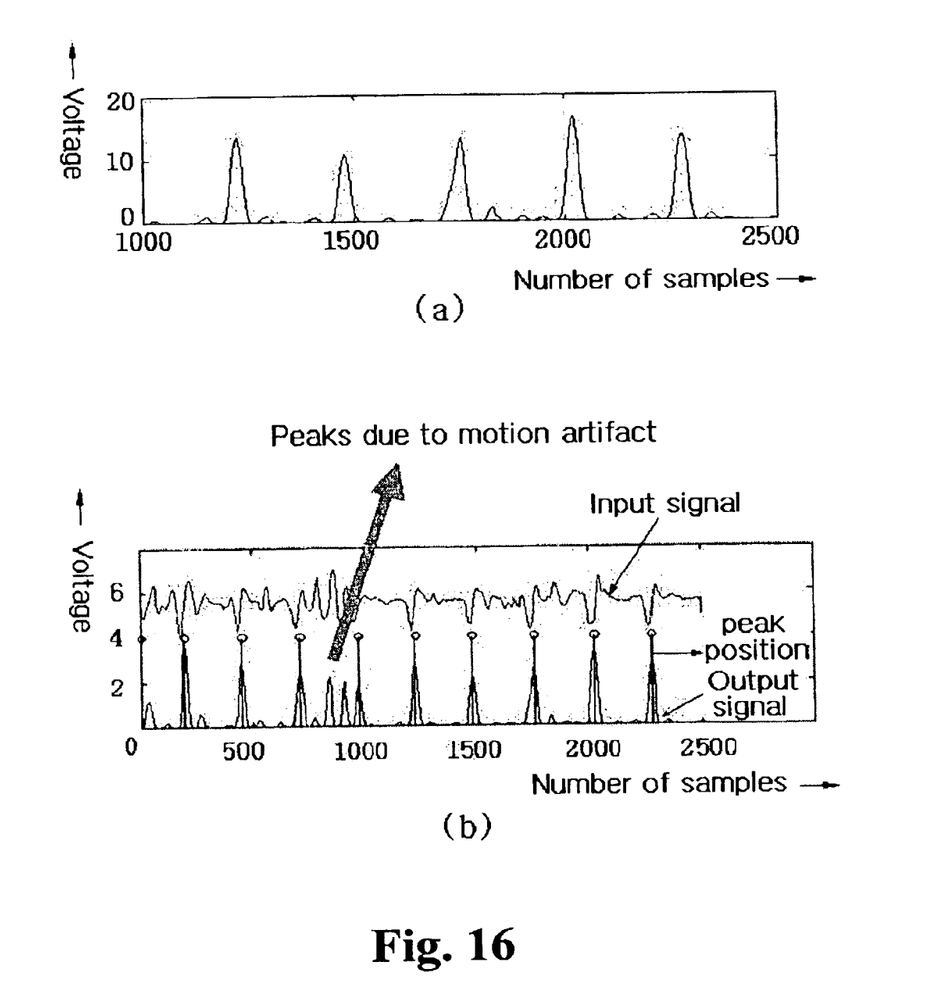
FIG. 16(a) is a waveform graph of a PPG signal with the motion artifacts being not included therein, which is inputted from the convolution unit to the heartbeat sequence/mean heart rate extraction unit.
FIG. 16(b) is a waveform graph of a PPG signal with the motion artifacts being included therein, which is inputted from the convolution unit to the heartbeat sequence/mean heart rate extraction unit.

First, the hard thresholded PPG signal is wavelet transformed and is decomposed into respective components corresponding to different scales. Then, as shown in FIG. 15 (a), the approximation signal component a5 representing the overall waveform of the signal and the detail signal components d1, d2, d3, d4 and d5 are obtained (step S151).

In the second hard thresholding part 75, the small-amplitude components of the detail signals generated through the wavelet transformation are discarded while only the other large-amplitude components thereof are extracted, so that the high frequency noise can be removed (step S152). A hard thresholding level used to this end is expressed as the following equation (4).

$$Th2 = b \times \max(\text{input}) \tag{4}$$

where $0.7 \leq b < 1.0$

Then, as shown in FIG. 15(b), the PPG signal is approximated by combining the approximation signal generated through the wavelet transformation with the detail signals subjected to the hard thresholding process (step S153). Here, as described above, only the detail signal (e.g., d5) related to subtle change in the heartbeat, with the detail signals (e.g., d1, d2, d3 and d4) in the high frequency region excluded therefrom, may be selected as the detail signals to be combined with the approximation signal.

In the step of approximating the PPG signal (step S150), the PPG signal can be approximated by removing the high frequency noise. However, since the detail signals are subjected to the hard thresholding process when combining the detail signals with the approximation signal, the discontinuous points exists in the approximated signal (refer to FIG. 15(b)). Thus, in order to remove the discontinuous points from the approximated signals, the zero clipping of the approximated PPG signal is performed so that the signal components irrelevant to the heartbeat are removed (step S170). Further, the zero clipped PPG signal is convoluted with the Bartlett window function so that the PPG signal is smoothed. Accordingly, the discontinuous points due to the approximation process are removed (step S190).

Furthermore, the optimal heartbeat sequence/mean heart rate can be extracted by maximally suppressing the influence of the motion artifacts on the approximated PPG signal (step S210). Hereinafter, a process of detecting the heartbeat sequence/mean heart rate will be more specifically explained with reference to FIG. 9.

Figure 9:
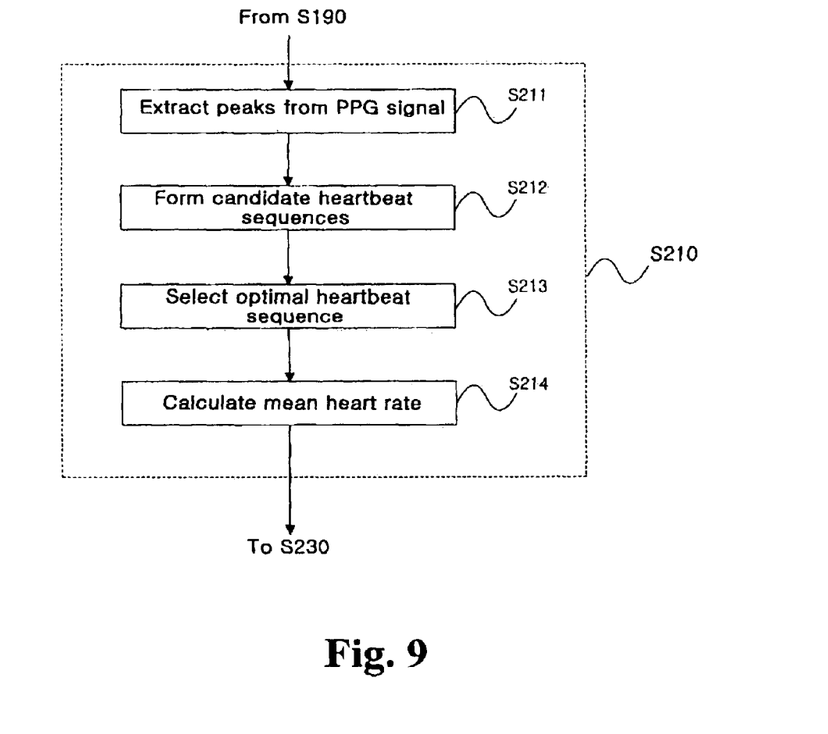
FIG. 9 is a detailed flowchart illustrating a step of extracting a heartbeat sequence/means heart rate shown in FIG. 7.
Figure 17:
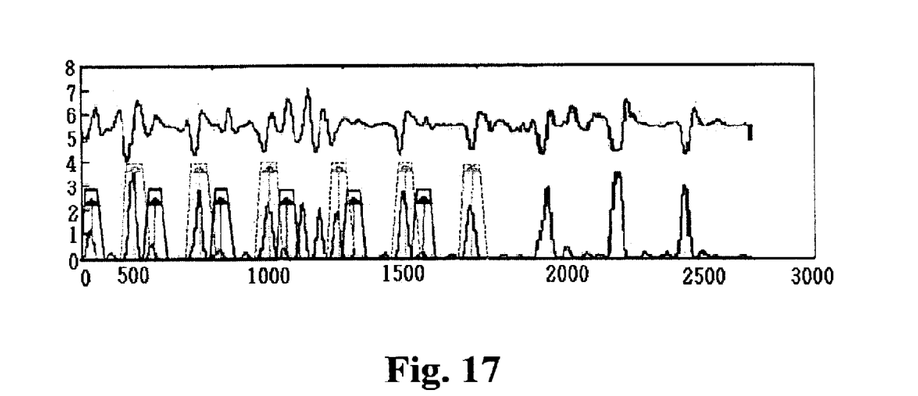
FIG. 17 is a waveform graph illustrating a method of selecting the optimal heartbeat sequence among candidate heartbeat sequences.

First, all the peaks existing within the initial interval (the interval within about two seconds) are detected from the approximated PPG signal (step S211), and then, the plurality of the candidate heartbeat sequences starting from the respective peaks existing within the initial interval are formed (step S212) (refer to FIG. 17). At this time, the candidate heartbeat sequences mean a series of sequences formed by sequentially detecting or extracting the starting peaks and the peaks existing within a range of IBI±ΔT from the relevant starting peak to an end of the analysis interval.

Here, the expected mean interbeat interval (mean IBI), which is calculated from the mean interbeat interval estimating part 79, is used when forming the candidate heartbeat sequences. Hereinafter, a step S140 of estimating the expected mean interbeat interval will be more specifically explained with reference to FIG. 10.

Figure 10:
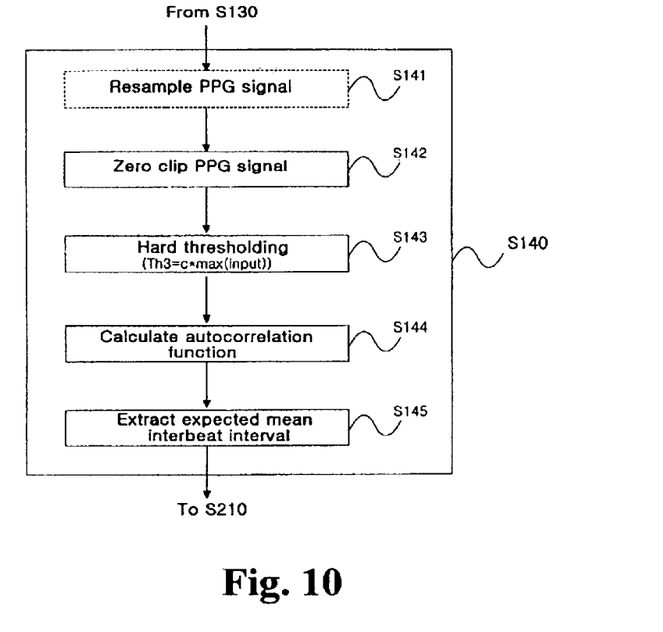
FIG. 10 is a detailed flowchart illustrating a step of estimating a mean heart rate time shown in FIG. 7.

First, the inputted PPG signal is resampled in order to remove the undesired high frequency components therefrom (step S141), and then, the zero clipping of the resampled PPG signal is made so that only the peak components due to the heartbeat can be outputted (step S142).

Then, the hard thresholding of the zero clipped PPG signal is made so that only the peaks related to the heartbeat can be extracted (step S143). Here, a hard thresholding value is expressed as the following equation (5).

$$Th3 = c \times \max(\text{input}) \tag{5}$$

In the embodiment of the present invention, the hard thresholding value Th3 has been set as a c-times value of the maximum value of the PPG signal within the interval. Further, since the signal lower than the hard thresholding level Th3 is not a peak due to the heartbeat, it is ignored and removed as an undesired signal.

Then, after the autocorrelation function of the hard thresholded PPG signal is calculated (step S144), a time τ when a first peak occurs is detected from the autocorrelation function of the noise-removed PPG signal so that the time is extracted as the expected mean interbeat interval (step S145) (refer to FIG. 18).

Here, the reason that the expected mean interbeat interval is extracted from the mean interbeat interval estimating part 79 is that the candidate heartbeat sequences can be formed in a short time through the peak detection from only the interval where the heartbeat occurring probability is high.

If there are two or more peaks in the interval of mean IBI±ΔT when forming the candidate heartbeat sequences, the peak close to the expected mean interbeat interval mean IBI is selected. If there is no peak in the interval or the peak amplitude is too small (i.e., it is third tenth times smaller than the maximum peak amplitude within the initial two-second interval), the candidate heartbeat sequences are formed after expanding an interval range of ΔT by a predetermined increment. In the embodiment of the present invention, the range may be increased by five samples, i.e. by 0.2 second (five samples/25 Hz) in view of time.

Figure 11:
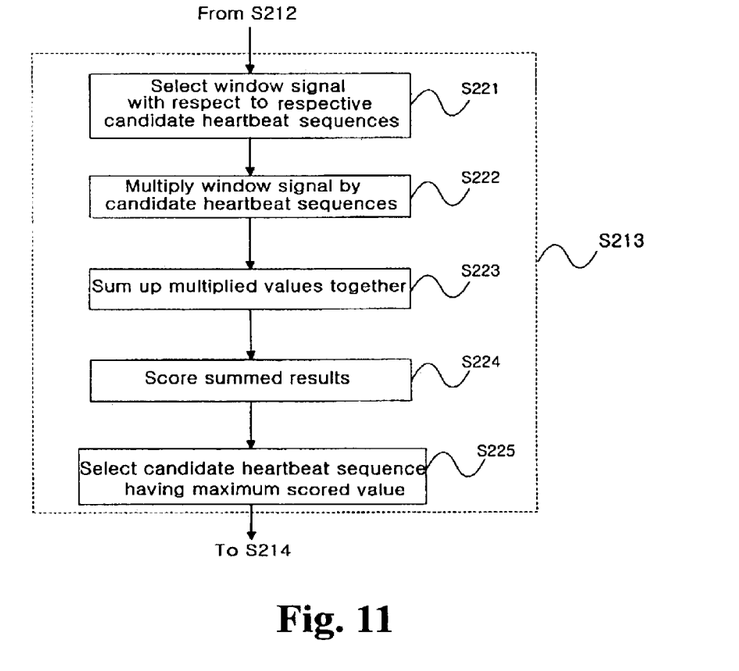
FIG. 11 is a detailed flowchart illustrating a step of selecting an optimal heart rate sequence shown in FIG. 9.

Then, the respective candidate heartbeat sequences are scored and the optimal heartbeat sequence is selected based on the scored values (step S213), which will be more specifically explained hereinafter with reference to FIG. 11.

First, the window signals are selected in such a manner that the respective peaks are within the initial interval (the interval of about two seconds) selected in the aforementioned step S212 of forming the candidate heartbeat sequences are set as the starting points and then points spaced apart from the starting points by the expected mean interbeat interval mean IBI are set as center points (step S221) (refer to FIG. 17). That is, the window signals are selected to be centered on a time spaced apart by the expected mean interbeat interval sequentially from the same starting points as the candidate heartbeat sequences, and the widths thereof may be selectively changed. In the embodiment of the present invention, the widths of the window signals are set to be 2×ΔT.

Then, the window signals and the candidate heartbeat sequences of which starting points are the same as the window signals are multiplied by each other, and all the multiplied values are summed up together (steps S222 and S223). The summed values are scored, and the candidate heartbeat sequence having the maximum scored value is selected as the optimal heartbeat sequence (steps S224 and S225) (referring to FIG. 17). As described above, the solid and dashed arrows and trapezoids shown in FIG. 17 correspond to the times spaced apart by the expected mean interbeat interval from the starting points of the two candidate heartbeat sequences and the window signals of which centers are positioned at the times, respectively. Here, the second candidate heartbeat sequence is selected as the optimal heartbeat sequence.

Finally, a time when the heartbeat occurs is displayed on the screen based on the optimal heartbeat sequence selected in the step S213. Otherwise, a mean heart rate is calculated based on the time when the heartbeat occurs due to the heartbeat sequence within the predetermined interval (step S214), and is displayed on the screen (step S230). Further, if other instructions to measure the heartbeats are inputted from the user, it goes into the PPG signal detection step; and otherwise, the heartbeat detection is terminated (step S250).

Figure 19:
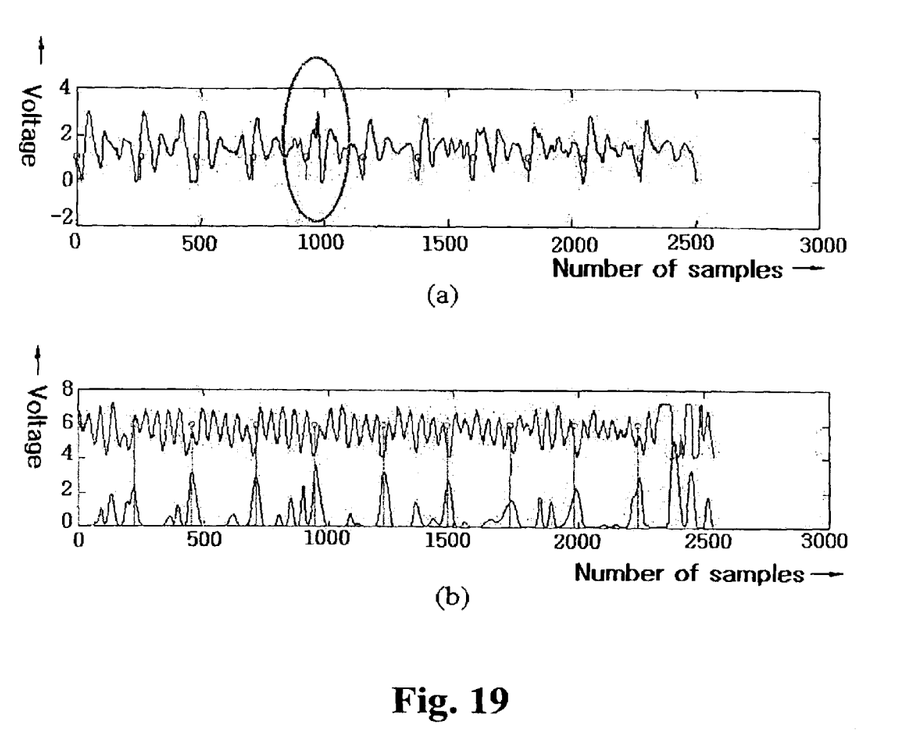
FIG. 19 is a waveform graph illustrating a result that an accurate heartbeat has been detected from the PPG signal with the motion artifacts being included therein according to the present invention.

FIG. 19 is a waveform showing that the correct heartbeat has been detected from the PPG signal including the motion artifacts according to the present invention. Even though the instantaneous peaks occur in the PPG signal due to the motion artifacts as shown in FIG. 19(a), the motion artifacts can be removed from the PPG signal according to the method of detecting the heartbeat according to the present invention. Thus, the heartbeat can be accurately detected as shown in FIG. 19(b).

According to the apparatus and method of detecting the heartbeat using the PPG, the heartbeat detection can be directly made without any reference signals contrary to the prior arts. Therefore, the present invention can be usefully employed in the medical or non-medical purpose instruments such as a sports watch having functions of diagnosing body conditions, a stress level measuring device, a caloric consumption measuring device, an emotion cognition device, a patient monitoring device, and an anesthetic level monitoring device.

Further, since the heartbeat can be efficiently detected from the PPG signal even under the motion of the user, the user does not feel reluctance and discomfort upon the heartbeat detection.

Although the present invention has been described in connection with the preferred embodiments thereof, they are mere examples of the present invention. It will be understood by a person skilled in the art various modifications, changes and equivalents thereof can be made thereto within the spirit of the present invention. Therefore, the true scope of the present invention should be defined by the appended claims.

What is claimed is:

1. An apparatus for detecting a heartbeat using a photoplethysmography (PPG), comprising:
   a sensor unit for detecting a PPG signal from a body of a user;
   a mean interbeat interval estimating unit for calculating an expected mean interbeat interval based on the detected PPG signal; and a heartbeat sequence/mean heart rate extracting unit for detecting candidate heartbeat sequences from the PPG signal using the expected mean interbeat interval and extracting an optimal heartbeat sequence or a mean heart rate from the candidate heartbeat sequences.

2. The apparatus as claimed in claim 1, wherein the mean interbeat interval estimating unit includes a hard thresholding part for hard thresholding the PPG signal with a predetermined level, an autocorrelation part for calculating an autocorrelation value of the hard thresholded PPG signal, and a peak detecting part for detecting a time when a first peak occurs from the autocorrelation value.

3. The apparatus as claimed in claim 2, wherein the predetermined hard thresholding level of the hard thresholding part is expressed as 0.5×max(input).

4. The apparatus as claimed in claim 2, wherein the mean interbeat interval estimating unit further includes a clipping part for clipping the PPG signal based on a predetermined level.

5. The apparatus as claimed in claim 1, wherein the heartbeat sequence/mean heart rate extracting unit includes a peak detecting part for detecting peaks from the PPG signal, a candidate heartbeat sequence forming part for forming a plurality of the candidate heartbeat sequences based on the detected peaks, a heartbeat sequence selecting part for selecting the optimal heartbeat sequence among the plurality of the candidate heartbeat sequences, and a mean heart rate calculating part for calculating the mean heart rate using the optimal heartbeat sequences selected by the heartbeat sequence selecting part.

6. The apparatus as claimed in claim 1, further comprising a motion artifact level determining unit for determining a level of a motion artifact in the PPG signal based on the PPG signal detected from the PPG sensor unit so that a warning message is produced when the level of the motion artifact is greater than a predetermined threshold value.

7. The apparatus as claimed in claim 6, further comprising a display unit for displaying both the optimal heartbeat sequence or mean heart rate extracted from the heartbeat sequence/mean heart rate extracting unit and the warning message produced from the motion artifact level determining unit.

8. The apparatus as claimed in claim 6, wherein the motion artifact level determining unit includes a TEO operating part for calculating an output value related to a rate of change in an amplitude or frequency of the PPG signal, a convolution part for convoluting a signal outputted from the TEO operating part with a predetermined window function, and a motion artifact threshold measuring part for performing a hard thresholding process of a signal inputted from the convolution part based on the predetermined level of the motion artifact so that the warning message is produced when the hard thresholded signal is greater than the threshold value.

9. The apparatus as claimed in claim 1, further comprising a filtering unit for selectively passing only a signal within a specific frequency band among the PPG signal detected by the PPG sensor unit.

10. The apparatus as claimed in claim 1, further comprising a PPG signal approximating unit for decomposing the PPG signal detected from the PPG sensor unit into an approximation signal and detail signals at different scales using wavelet transformation and combining the approximation signal and the detail signals greater than a predetermined threshold value so that a resultant approximated signal can be generated.

11. The apparatus as claimed in claim 10, wherein the PPG signal approximating unit includes a wavelet transforming part for decomposing the PPG signal into the detail signals and the approximation signal through wavelet transformation, a second hard thresholding part for extracting only the signal greater than the predetermined threshold value among the detail signals generated through the wavelet transformation, and a signal combining part for combining the signal greater than the predetermined threshold value with the approximation signal generated through the wavelet transformation.

12. A method of detecting a heartbeat using a photoplethysmography (PPG), comprising the steps of:
(a) detecting a PPG signal received from a user through a PPG sensor unit;
(b) calculating an expected mean interbeat interval (mean IBI) from the PPG signal; and
(c) detecting determining an optimal heartbeat sequence or mean heart rate from candidate heartbeat sequences which have been detected from the PPG signal using the expected mean interbeat interval.

13. The method as claimed in claim 12, wherein the step (b) comprises the steps of:
(b1) performing a hard thresholding process of the PPG signal on the basis of a predetermined level;
(b2) calculating an autocorrelation function value of the hard thresholded PPG signal; and
(b3) detecting a time when a first peak of the autocorrelation function value occurs.

14. The method as claimed in claim 13, wherein the predetermined hard thresholding level is expressed as 0.5× max(input).

15. The method as claimed in claim 13, wherein the step (b) further comprises the step of clipping the PPG signal with a predetermined level.

16. The method as claimed in claim 12, wherein the step (c) comprises the steps of:
(c1) detecting peaks from the PPG signal;
(c2) forming a plurality of candidate heartbeat sequences based on the detected peaks;
(c3) selecting the optimal heartbeat sequence among the plurality of candidate heartbeat sequences; and
(c4) calculating the mean heart rate based on the heartbeat sequences selected by the heartbeat sequence selecting part.

17. The method as claimed in claim 16, wherein the step (c2) comprises the steps of:
(c2-1) selecting respective peaks within a predetermined period of time as starting points; and
(c2-2) selecting peaks within intervals sequentially spaced apart from the starting points by a value of mean IBI±ΔT and then setting the selected peaks as the plurality of candidate heartbeat sequences.

18. The method as claimed in claim 17, wherein the step (c2-4) comprises the steps of:
selecting a peak close to the expected mean interbeat interval if there are a plurality of peaks within the intervals sequentially spaced apart from the starting point by the value of mean IBI±ΔT; and
expanding an interval range of ΔT by a predetermined increment if there are no peaks within the intervals spaced apart from the starting points by the value of mean IBI±ΔT or the signal is lower than a predetermined value.

19. The method as claimed in claim 17, wherein the step (c3) comprises the steps of:
selecting window signals sequentially spaced apart from the selected starting points by a value of mean IBI; and selecting the optimal heartbeat sequence by combining the window signals with the candidate heartbeat sequences having the same starting points as the window signals and then comparing combined results thereof with one another.

20. The method as claimed in claim 12, further comprising the step of:
   (d) determining a level of a motion artifact based on the PPG signal detected from the PPG sensor unit and then generating a warning message when the level of the motion artifact is greater than a predetermined threshold value.

21. The method as claimed in claim 20, further comprising the step of:
   (e) displaying the detected optimal heartbeat sequence or mean heart rate and the warning message on a screen.

22. The method as claimed in claim 20, wherein the step (d) comprises:
   (d1) a TEO operating step of calculating a sudden rate of change in an amplitude and frequency of the PPG signal;
   (d2) a convolution step of convoluting the signal outputted from the step (d1) with a predetermined window function; and
   (d3) a warning message generating step of performing the hard thresholding process of the convoluted signal on the basis of a predetermined level and then generating a warning message when the hard thresholded signal is greater than me predetermined threshold value.

23. The method as claimed in claim 12, further comprising:
   (f) a filtering step of selectively passing only a signal within a specific frequency band among the PPG signal detected by the PPG sensor unit.

24. The method as claimed in claim 12, further comprising the steps of:
   (g) decomposing the PPG signal detected from the PPG sensor unit into an approximation signal and detail signals through wavelet transformation; and
   (h) combining the approximation signal and the detail signals greater than a predetermined threshold value so that a resultant approximated signal can be generated.

25. The method as claimed in claim 24, wherein the step (h) comprises:
   (h1) a hard thresholding step of extracting only the signal greater than the predetermined threshold value among the detail signals generated through the wavelet transformation; and
   (h2) a signal combining step of combining the approximation signal with the detail signal extracted from the step (h1) and greater than the predetermined threshold value.

* * * * *